United States Patent
Buckley et al.

(10) Patent No.: US 7,475,591 B2
(45) Date of Patent: Jan. 13, 2009

(54) METHODS AND SYSTEMS FOR HYDROSTATIC TESTING A PIPELINE

(75) Inventors: Wade S. Buckley, Houston, TX (US); Eric N. Freeman, Sapulpa, OK (US); Larry D. Payne, Tulsa, OK (US); Kim R. Stover, Tulsa, OK (US)

(73) Assignee: TDW Delaware, Inc., Wilmington, DE (US)

( * ) Notice: Subject to any disclaimer, the term of this patent is extended or adjusted under 35 U.S.C. 154(b) by 311 days.

(21) Appl. No.: 11/284,620

(22) Filed: Nov. 22, 2005

(65) Prior Publication Data

US 2007/0113622 A1     May 24, 2007

(51) Int. Cl.
  *G01M 3/04*   (2006.01)
  *G01M 3/28*   (2006.01)
(52) U.S. Cl. ............................. 73/49.5; 73/37
(58) Field of Classification Search .................. 73/49.5, 73/37, 49.4, 826, 831, 834
  See application file for complete search history.

(56) References Cited

U.S. PATENT DOCUMENTS

| | | | |
|---|---|---|---|
| 3,746,026 A | 7/1973 | Herring | |
| 3,750,711 A | 8/1973 | Conklin et al. | |
| 3,837,214 A | 9/1974 | Guest | |
| 3,908,682 A | 9/1975 | Thompson | |
| 4,026,329 A | 5/1977 | Thompson | |
| 4,314,577 A | 2/1982 | Brister | |
| 4,441,328 A | 4/1984 | Brister | |
| 4,484,602 A | 11/1984 | Guthrie | |
| 4,691,728 A | 9/1987 | Mathison | |
| 4,854,384 A | 8/1989 | Campbell | |
| 4,872,336 A * | 10/1989 | Baillie | 73/40.5 R |
| RE33,160 E | 2/1990 | Guthrie et al. | |
| 4,991,651 A | 2/1991 | Campbell | |
| 5,029,614 A * | 7/1991 | Lara et al. | 138/90 |
| 5,139,576 A | 8/1992 | Davis | |
| 5,272,646 A | 12/1993 | Farmer | |
| 5,372,162 A | 12/1994 | Frey | |
| 5,433,236 A | 7/1995 | Zollinger et al. | |
| 5,842,816 A | 12/1998 | Cunningham | |

(Continued)

OTHER PUBLICATIONS

International Search Report and Written Opinion; dated Apr. 22, 2008; issued by International Searching Authority ISA/US; 11 pages.

*Primary Examiner*—David A. Rogers
(74) *Attorney, Agent, or Firm*—Gable Gotwals (57) ABSTRACT

A method of hydrostatic testing a selected section of a pipeline having fluid flow therethrough, including the steps of introducing into the pipeline a pig train including a leading seal pig, a supply liquid slug, a first isolation tool, a test liquid slug and a second isolation tool; permitting the train to traverse the pipeline interior by the force of fluid flow until the lead isolation tool is forwardly of and the second isolation tool is rearwardly of the selected selection of the pipeline; securing the position of the pig train by applying exteriorly of the pipeline appropriate signals to actuate the isolation tools to each engage and seal the interior of the pipeline trapping the test liquid slug therebetween; and pumping liquid from the supply liquid slugs into the test liquid slug to a hydrostatic testing pressure. In addition to testing, the pipeline can be repaired by moving the pig train into position where a defective area can be isolated by additional isolation tools.

41 Claims, 5 Drawing Sheets

U.S. PATENT DOCUMENTS

| | | |
|---|---|---|
| 5,983,948 A | 11/1999 | Yagi et al. |
| 6,022,421 A | 2/2000 | Bath et al. |
| 6,348,869 B1 | 2/2002 | Ashworth |
| 2004/0200019 A1 * | 10/2004 | Pruett .................... 15/104.061 |

* cited by examiner

METHODS AND SYSTEMS FOR HYDROSTATIC TESTING A PIPELINE

REFERENCE TO PENDING APPLICATIONS

This application is not based upon any pending domestic or international patent applications.

REFERENCE TO MICROFICHE APPENDIX

This application is not referenced in any microfiche appendix.

BACKGROUND OF THE INVENTION

1. Field of the Invention

This invention relates to methods for hydrostatic testing a section of a pipeline that employs a pig train including plugging tools, at least one sealing pig, slugs of fluid between the sealing pig and plugging tools and a pumping system for increasing the hydrostatic pressure interior of the pipeline between spaced apart plugging tools.

2. Description of the Prior Art

The invention herein discloses methods and systems for hydrostatic testing a pipeline.

In North America, Europe and other industrialized areas of the world, vast quantities of fluids, including liquids and gases, are transported through pipelines. These fluids include crude oil, lubricating oil, natural gas, gasoline and so forth. These pipelines are often of considerable length and extend over all types of geographic terrains. Many pipelines today are located underneath rivers and lakes and growing mileages of pipelines are located on the surface of the earth covered by seawater, that is, submerged or subsea pipelines.

In the event of damage, deterioration from age, or changing conditions including need for modification or structural changes to a pipeline, a serious problem rises as to the manner in which the flow of liquid, either fluid or gases, through the pipeline can be controlled during repair, maintenance and testing. Most pipelines in use today are continuously filled with liquids or gases. Since the volume contained in a relatively long length of pipeline is great, the value of the contained fluid is great. In addition, in most instances if it is necessary to repair, replace or test a pipeline it is not feasible to drain the pipeline due not only to the cost of the contents but many of the products carried by pipelines are deleterious to the environment. Many governmental restrictions around the world prohibit discharging pipeline contents into the environment for the purpose of facilitating repair, maintenance or testing.

One method used to test or repair a pipeline is to isolate and evacuate a section of the pipeline by using internally transportable plugging devices or pigs. In order to employ a plugging pig it is necessary to be able to stop the pig at a preselected location and by internal means, closing the plugging pig to seal the interior of the pipeline against further fluid flow. When repair, maintenance, testing or so forth is completed, it is then necessary to release the grip of the plugging pig to permit it to resume passage through the interior of the pipeline by the force of fluid flow. In this way, the plugging device in the form of a fluid transportable pig, can be removed from the pipeline after its use has been completed and the pig reused for further applications.

A commonly used method to stop flow in a pipeline temporarily is by the utilization of a product commercially available under the trademark STOPPLE® as manufactured and supplied by T.D. Williamson, Inc. of Tulsa, Oklahoma. A method of use of the STOPPLE® plugging system includes installing an access fitting followed by boring a large diameter hole at each of two extremities of the pipeline to be worked on or tested, inserting a plug in each large hole and pivoting the plug about a transverse axis to plug the pipe. After the repair work is done, the plugs are pivoted back and removed from the hole and large flanges are secured on the fittings. While this system functions successfully in areas where the pipe is readily accessible from the earth's surface, in many locations accessibility is a continuous problem and this is particularly a burdensome problem with pipelines running under lakes, rivers and especially pipelines running on the ocean floor. For this reason and in recent years plugging tools or plugging pigs have been developed. These devices are insertable in the pipeline for movement by fluid flow and can be actuated at a selected point to grip the interior wall while simultaneously sealing the interior wall of the pipeline against fluid flow. The invention herein includes methods, systems and devices for employing such plugging pigs in pipelines particularly for hydrostatic testing of pipelines.

For additional information relating to the background of the subject matter of this invention, reference may be had to the following United States patents and publications:

| Patent Number | Inventor | Title |
| --- | --- | --- |
| RE33,160 | Guthrie et al. | Method and Apparatus For Inspecting Lateral Lines |
| 3,746,026 | Herring | Pipeline Plugging Pig |
| 3,750,711 | Conklin et al. | Method and Apparatus For Testing For Leaks In Pipes |
| 3,837,214 | Guest | Self-Propelled Pipeline Plug |
| 3,908,682 | Thompson | Methods and Apparatuses For Remotely and Releasably Sealing A Pipe Line |
| 4,026,329 | Thompson | Method and Apparatus For Remotely and Releasably Sealing A Pipeline |
| 4,314,577 | Brister | Installation, Hydrostatic Testing, Repair and Modification of Large Diameter Fluid Transmission Lines |
| 4,441,328 | Brister | Method and Apparatus For Forming A Temporary Plug In A Submarine Conduit |
| 4,484,602 | Guthrie | Packer For Sealing Lateral Lines |
| 4,691,728 | Mathison | Electronic Test and Seal Apparatus and Method |
| 4,854,384 | Campbell | Pipeline Packer |
| 4,991,651 | Campbell | Pipeline Packer For Plugging A Pipeline At A Desired Location |
| 5,139,576 | Davis | Method and A Horizontal Pipeline Pig Launching Mechanism For Sequentially Launching Pipeline Pigs |
| 5,272,646 | Farmer | Method For Locating Leaks In A Fluid Pipeline and Apparatus Therefore |
| 5,372,162 | Frey | Repair Device For The In Situ Repair of Pipes, And A Method of Repairing Pipes |
| 5,433,236 | Zollinger et al. | Apparatus For Moving A Pipe Inspection Probe Through Piping |
| 5,842,816 | Cunningham | Pig Delivery and Transport System For Subsea Wells |
| 5,983,948 | Yagi et al. | Method of Repairing An Existing Pipeline Including A Main Pipe and A Branch Pipe |
| 6,022,421 | Bath et al. | Method For Remotely Launching Subsea Pigs In Response To Wellhead Pressure Change |
| 6,348,869 | Ashworth | Pipe Leak Detection |

BRIEF SUMMARY OF THE INVENTION

The methods and systems of this invention for testing a length of a pipeline includes the use of at least two isolation tools introduced into the pipeline. The isolation tools having means for being propelled by fluid flow (liquid or gas) through the pipeline. Further, the isolation tools have means by which they may be set at selected locations and actuated for sealing the pipeline against fluid flow therethrough. Specifically the isolation tools each have facilities for receiving a signal applied from the exterior of the pipeline to initiate the steps required for gripping the interior of the pipeline to stop movement through the pipeline and for sealing the interior of the pipeline against fluid flow.

A sealing pig is introduced in the pipeline a pre-selected time or distance prior to the introduction of the first isolation tool. The sealing pig is typically a pig that does not include moving parts or communication systems but includes only cups or discs that extend from a central body to slidably engage the interior wall of the pipeline. The cups or discs of the sealing pig slide on the interior of the pipe wall as moved along by fluid flow. When the fluid flow stops, the sealing pig stops since it has no means of locomotion. Further, the sealing pig has no means whereby it can be commanded to stop nor can the speed of movement of the sealing pig be effected by externally applied signals since the sealing pig is solely controlled by the speed of movement of the fluid through the pipeline.

After a sealing pig is introduced into a pipeline, such as by the use of a pig launcher, the interior of the pipeline may be filled with a selected fluid that is different from the fluid normally flowing through the pipeline. For instance, after a sealing pig is introduced a quantity of fluid, such as water, can be introduced into the pipeline. This fluid that is introduced into the pipeline and that is different from the fluid or gas that is normally flowing through the pipeline is referred to as a "first testing liquid slug". After the pre-selected quantity of the liquid slug is introduced into the pipeline, then the first isolation tool is immediately introduced.

After the first isolation tool is introduced, a time delay or liquid volume displacement occurs before a second isolation tool is introduced. The spacing between the first and second isolation tools is selected in accordance with the time delay or liquid volume displacement of launching the second isolation tool. That is, the speed of travel of the liquid in the pipeline multiplied by the time of delay between launching the first and second isolation tool, or a measured volume of liquid is pumped, thereby determines the spacing between the two isolation tools. This spacing can vary according to the intended purpose. When the purpose is to hydrostatically test a portion of the length of a pipeline, the spacing between the isolation tools equal to the length of the pipeline to be hydrostatically tested. This can vary from a few feet to several miles.

After the second isolation tool is introduced into the pipeline in a preferred practice of the invention a second or follow up slug of liquid is introduced into the pipeline in a quantity as required for the procedure to be employed. After the required follow up slug of liquid is introduced into the pipeline, a trailing seal pig is launched into the pipeline.

Thus the basic system of this invention is a pig train made up of a lead seal pig, a leading liquid slug, a lead or first isolation tool, a test liquid slug and a second isolation tool and a trailing seal pig, if needed. Thus, in addition to the pigs making up a basic train for use in practicing the invention, that is a seal pig and two isolation tools, the train includes a leading liquid slug between the leading seal pig and the leading plug pig and a test slug between the two isolation tools.

The system further includes a pump for pumping liquid from the leading liquid slug past the lead isolation tool and into the test slug. When the system is used for a pipeline located on the earth's surface, the pump can be located exteriorly of the pipeline. To provide access from the pump to the interior of the pipeline, small diameter branch fittings are secured to the pipeline, such as by welding, and then by using a hot tapping system the pipeline is penetrated. This can be accomplished while the pipeline is under pressure by employing hot tapping equipment illustrated and described in the following patents:

| Patent Number | Inventor | Title |
|---|---|---|
| 4,579,484 | Sullivan | Underwater Tapping Machine |
| 4,880,028 | Osburn et al. | Completion Machine |
| 5,439,331 | Andrew et al. | High Pressure Tapping Apparatus |
| 6,012,878 | Hicks | Pressure Balanced Subsea Tapping Machine |
| 6,648,562 | Calkins et al. | Apparatus For Tapping A Hole In A Pipeline |

Instrumentation is contained in a control module portion of at least one of the isolation tools for measuring and recording fluid pressure in the test section to provide the hydrostatic testing information obtained by the use of the system of the invention. Each isolation tool as employed in the invention will consist of at least three sections, including a gripper module, a packer module and an instrument module. The gripper and packer modules typically include hydraulic cylinders and therefore a source of hydraulic fluid pressure is employed in each isolation tool.

The invention herein uses a pig train formed of a combination of isolation tools (plugging pigs), batching pigs, and liquid batches, also referred to as "slugs", which can be propelled along inside the pipeline. This test "train" can be set, a hydrostatic test performed and the train moved along to the next position, and the whole sequence repeated, without the need for welding on test heads, filling the pipeline with test medium, draining the pipeline of test medium and removing the test heads—as in a conventional hydro-testing approach. Therefore, the concept of this invention has the benefit of faster and/or lower cost pipeline hydrostatic testing. The invention herein makes it possible to hydrostatically test relatively short sections of a new pipeline just behind the pipe welding crew during the construction process—resulting in commissioning of new pipelines sooner than by conventional testing methods.

With an additional isolation tool in the pig train, an in-service pipeline can be hydrostatically tested and leaking or failed sections can be repaired while maintaining operating pressure in the pipeline, eliminating the need to completely remove the pipeline from service and without draining down or blowing down the pipeline to remove product therefrom.

The methods of this invention may be used for post-construction proof that a pipeline is capable of withstanding the intended design or operating pressure. Another purpose for this invention may be to qualify an in-service pipeline for an increase in operating pressure over what it has been operating at heretofore in the event the pipeline requires re-rating. The methods of this invention are useful for pipeline hydrostatic testing to meet governmental or industrial code requirements, as well as for insuring general safe operating practices.

A section of a pipeline may be hydrostatically tested and isolated for repair, using a "pig train" (a combination of isolation tools and batching pigs), in relatively short or long sections. The "isolation tools" referred to in this document may also be termed "plugging pigs" and are special purpose "smart" pipeline pigs that are designed to travel along in the pipe, propelled by the flow of product (by pumping or compression), stopped at selected locations and activated by a through-the-pipe-wall communication device to engage the inside diameter of the pipeline with grips and packers to hold back pressure in the pipeline. The isolation tools can then be commanded to release, following equalization of pressure, by external communication devices. "Seal pigs" as referred to herein may be termed "batching pigs" and are designed to provide a tight seal with the pipe wall while traveling along inside a pipeline as propelled by fluid flow and to contain a "batch" or "slug" of fluid that may be of a different type than that within the pipeline ahead or behind the pig train.

The basic configuration of the hydrostatic testing plugging pig train consists of a sealing pig in front, followed closely by a lead isolation tool with a short "make-up" batch or slug of test medium (water or other incompressible fluid) in between. The lead isolation tool is followed by any practical length of test medium and a second isolation tool oriented in the opposite direction in order to hold test pressure in the test section when both isolation tools are set and their packers energized. The length of this test section can be determined by taking into consideration testing time, hold time (for leak detection), elevation changes of the pipeline, which can result in variation of pressure along the test section, and other factors.

A problem exists with elevation changes in that when using water or other liquid as the test medium, pressure will vary significantly with elevation change (approximately 15 psi for every 33 feet of elevation due to the effect of gravity or "head") along the length of the test medium slug. This may limit the length of the test section due to the possibility of over pressuring the pipeline by the packer module.

In the case of new construction where there is no need to isolate operating pressure during repairs of failed or leaking sections, the trailing isolation tool may be followed closely by another seal pig with a slug of make-up test medium in between. In the case of an operating pipeline, where a defective section of pipeline needs to be isolated from operating pressure during repair, a third isolation tool may follow the second isolation tool by some practical distance with a slug of test medium in between primarily to maintain a fixed distance behind the second isolation tool and to prevent a compressible gas "bubble" from seeping into the test section.

The main purpose of the make-up media is to provide make up volume during test pressurization and to prevent a compressible gas "bubble" from seeping into the test or isolation media. Another purpose of the trailing "make up" slug is to carry a fluid such as methanol or glycol to allow drying of an on-stream gas line while the pig train moves along. The hydrostatic test slug (water or mostly water) leaves a wet pipe wall which results in gradual loss of test medium volume as the train moves down the pipe. This make-up slug can serve the dual purpose of providing make-up medium and drying the line behind the test train.

As previously stated, pumping up the test section utilizes hot-tapping with two small pipe nipples welded to the pipe on either side of an isolation tool with a pumping manifold installed in between by way of temporary external piping. This manifold transfers test medium from a leading slug during pressure testing and returns it to the leading slug during depressurization. Test pressure pumping may also be accomplished by the use of on-board pumping capabilities with a passageway through an isolation tool to transfer liquid into the test section.

If a leak is discovered and located in an operating pipeline, the pig train of this invention can be advanced until the leak is straddled by an isolation section of the train. The isolation tools to either side of the leak can be set and the isolated section of pipe containing the leak can be depressurized and repaired without draining or venting product beyond the relatively short isolated section. After repairs, the isolation tools can be unset and the train moved along to the next test section.

Because of the chance of having a rupture during hydrostatic testing of an operating pipeline, an additional isolation tool may be included to block ambient pipeline pressure downstream of the pig train while a different isolation tool can be set to block ambient pipeline pressure upstream of the pig train. In this case, the additional isolation tool prevents the dislodging and movement of the other isolation tools toward the rupture, possibly saving damage and loss of much or all of the hydrostatic test media. This extra step may be necessary because isolation tools typically only hold pressure in one direction and may be dislodged if pressure is reversed.

In a deep subsea environment a huge hydrostatic head exists on the outside of the pipeline so hydrostatic testing of the pipeline takes on different problems. When the pipeline in question is a gas line, the internal pressure may be low compared to the external pressure. The methods of this invention are advantageous in finding and isolating leaks. If two isolation tools are moved into a pipeline with a fluid slug between them, they can be set and let the external (ambient) hydrostatic head of the water column provide the test pressure. If a pressure rise occurs between the isolation tools, then a leak is present. In this case, since the external pressure is greater than the internal pressure the leak can be located and isolated without moving the pig train. The pipeline could then be repaired or a repair clamp installed for repair at a later date.

In the case where the gas pressure in a subsea pipeline is higher than the ambient pressure, a plugging pig train with two outward looking isolation tools with a slug of water between can be launched into the pipeline and moved along by the internal hydrostatic pressure of a surface riser water column balancing pressure with the external ambient pressure, and with gas at a higher pressure than ambient sub-sea hydrostatic pressure on the other side of the pig train. In this case, the water column in the riser balances the ambient pressure while a hydrostatic pump at the surface is used to provide the testing pressure. The lead isolation tool is set, pressure is pumped up, the trailing isolation tool is set, pressure in the riser is released, resulting in test pressure remaining in the slug between the isolation tools. A sensed pressure drop would indicate a leak. Alternatively, an on-board pump can provide the additional test pressure between the isolation tools when set, eliminating pressure cycles in the riser.

A better understanding of the invention will be obtained from the following detailed description of the preferred embodiments and claims, taken in conjunction with the attached drawings.

BRIEF DESCRIPTION OF THE DRAWINGS

FIG. 1 is a diagrammatic cross-sectional view of a length of pipeline that is broken into three adjacent segments. This figure shows a pig train positioned within the pipeline, the pig train being made up of a leading isolation tool followed at a selectable distance by a second isolation tool. Preceding downstream within the pipeline of the lead isolation tool is a lead seal pig and trailing behind the second isolation tool is a trailing seal pig. Between the lead seal pig and the first isolation tool the pipeline is filled with a selected liquid and this quantity of liquid is identified as a leading liquid slug. Between the isolation tools the liquid within the pipeline is identified as a test slug. Following the second isolation tool and between it and the trailing seal pig is a quantity of liquid termed a "trailing liquid slug". Apparatus is provided by which elevated fluid pressure may be applied to the test slug to thereby hydrostatically test the pipeline.

FIG. 2 is a schematic representation of a length of pipeline broken in segments and shows a first alternate embodiment of practicing the invention. In FIG. 2 three isolation tools as well as leading and trailing seal pigs form four liquid slugs that are part of the total pipeline pig train.

FIG. 4 is a cross-sectional view of the major portions of a packer module as used in an isolation tool. The invention herein is not concerned with the details of construction of the packer module or of any of the pigs used in the systems. FIG. 4 is included only to indicate how a packer module portion of an isolation tool can function to seal the interior of the pipeline against fluid flow and to show piping that may be used to pass fluid to the test section in the case where an on-board pump is used. FIG. 4 is a cross-sectional view of a packer module as taken along the lines 4-4 of FIG. 1.

FIG. 6 is an enlarged cross-sectional view of the gripper module as taken along the line 6-6 of FIG. 5. FIG. 5 shows the gripper module located within a pipeline that is not shown in FIG. 6. As with the packer module, the details of the gripper module are not part of the present invention and the gripper module illustrated in the details of FIGS. 5 and 6 are intended only to be illustrative of the concept of an isolation tool that includes apparatus for locking itself in position within a pipeline and for closing the pipeline against flow therethrough, and for showing fluid transfer piping.

FIG. 7 is an elevational view of an isolation tool of the type that is illustrated in FIGS. 1 through 3 but shown in greater detail and with the increased elements as may be required in practicing some aspects of the invention. Particularly, FIG. 7 is illustrative of an isolation tool having multiple power modules formed in the train in combination with a packer module, a gripper module and a control module with fluid transfer piping. The embodiment of FIG. 7 is particularly important in one method of practicing the invention wherein hydrostatic testing of a portion of the length of a pipeline can be accomplished without the necessity of attaching piping fittings to the exterior of the pipeline.

DETAILED DESCRIPTION OF THE PREFERRED EMBODIMENTS

It is to be understood that the invention that is now to be described is not limited in its application to the details of the construction and arrangement of the parts illustrated in the accompanying drawings. The invention is capable of other embodiments and of being practiced or carried out in a variety of ways. The phraseology and terminology employed herein are for purposes of description and not limitation.

Elements illustrated in the drawings are identified by the following numbers:

| | |
|---|---|
| 10A, B, C | Pipeline sections |
| 12 | Lead seal pig |
| 14 | Lead isolation tool |
| 16 | Second isolation tool |
| 18 | Trailing seal pig |
| 20 | Leading liquid slug |
| 22 | Test liquid slug (hydro-test section) |
| 24 | Trailing liquid slug |
| 26A, B | Pipe nipples |
| 28A, B | Piping |
| 30 | Pumping manifold |
| 32 | Packer module |
| 34 | Universal joint (ball joint) |
| 36 | Gripper module |
| 38 | Universal joint (ball joint) |
| 40 | Control module |
| 42 | Elastomeric discs |
| 44 | Central body |
| 46 | Radial rails |
| 48 | Rail edge |
| 50 | Grip saddle |
| 52 | Inclined edge |
| 54 | Grip shoes |
| 56 | Gripping surface |
| 58 | Pipeline interior wall |
| 60 | Actuator body |
| 62 | Piston |
| 64 | Wheels |
| 66 | Coiled spring |
| 68 | Tubular body |
| 70 | External cylindrical surface |
| 72 | Fixed forward flange |
| 74 | Internal cylindrical wall |
| 76 | Cylindrical surface |
| 78 | Double ended piston rod |
| 80 | Rearward flange |
| 82 | Ball joint |
| 84 | Back up flange |
| 86 | External cylindrical surface |
| 88 | First elastomeric packer |
| 90 | Second elastomeric packer |
| 92 | Internal cylindrical surface |
| 94 | Contacting surface |
| 96 | Sidewall surfaces |
| 98 | Backup ring |
| 100 | Internal opening |
| 102 | Opposed sidewalls |
| 104 | Outer circumferential surface |
| 106 | Piston |
| 108 | Cylinder head |
| 110 | Opening |
| 112 | Cylindrical area |
| 116 | Rearward wheels |
| 118 | Forward wheels |
| 120 | First power module |
| 122 | Second power module |
| 124 | Universal joint |
| 126 | Universal joint |
| 128 | Flexible conduit |
| 130 | Flexible conduit |
| 132 | Third isolation tool |
| 134 | Isolation liquid slug |
| 136 | Fourth isolation tool |
| 138 | Second isolation liquid slug |
| 140 | Instrumentation |
| 142 | Actuation hydraulic pump |
| 144 | On-board test pump |
| 146 | On-board battery |
| 148 | Fluid inlet |
| 150 | Fluid outlet |

This invention provides systems and methods to test a portion of the length of a pipeline. The test can be of various types but basically constitute hydrostatic testing, that is testing the reaction of the pipeline to fluid pressure in the pipeline. Such tests can be made for many reasons. As an example, a length of a pipeline can be tested to see if there are leaks in the pipeline within the test section. The pipeline sections can be tested to determine whether it is capable of withstanding increased fluid pressure. This need arises frequently when pipelines that have been constructed and operated for several years are considered for upgrade to increase the flow rate which mandates increasing the pressure of fluid moving through the pipeline.

The invention herein makes use of devices that are sometimes referred to as "plugging pigs" but which will be referred to herein as "isolation tools". Pipeline pigs of this type typically are formed by a packer module in cooperation with a gripper module. These components can be manufactured separately and then joined to form an integral unit in which the components work in cooperation with each other. A "gripper module" means a section of the pipeline pig that can be actuated to grip against the interior wall of the pipeline and thereby lock the pig assembly into a temporarily fixed position in the pipeline. A packer module is an apparatus that can be expanded to close fluid flow through the pipeline.

Figure 1:
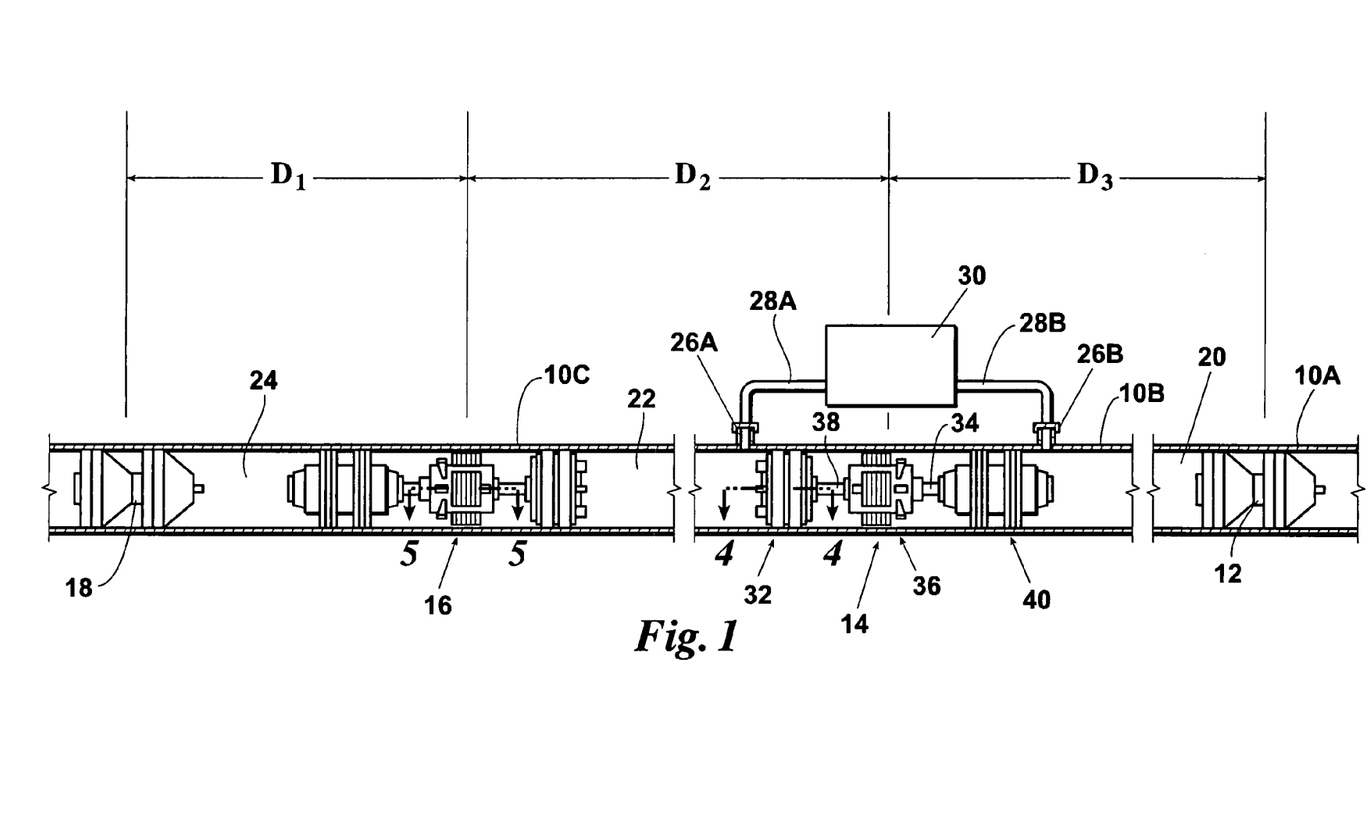

The system for practicing the invention is in the form of a train of elements introduced by a launching device into the interior of the pipeline. In FIG. 1, a section of a pipeline is illustrated, broken into sections 10A, 10B and 10C. The basic elements making up the pigging train illustrated in FIG. 1 is a lead seal pig 12 contained with pipeline section 10A; a lead isolation tool generally indicated by the numeral 14 contained in pipeline section 10B; a second isolation tool generally indicated by the numeral 16 contained in pipeline section 10C; and a trailing seal pig 18 that is also contained within pipeline section 10C.

In addition to the physical apparatus making up the train of components as illustrated in FIG. 1 for performing hydrostatic testing of the interior of the pipeline, a leading liquid slug 20 is introduced into the interior of the pipeline filling the space between lead seal pig 12 and lead isolation tool 14. Between lead isolation tool 14 and second isolation tool 16, there is a test slug 22, that is, a column of water traveling in the pipeline between the first and second isolation tools. Between second isolation tool 16 and trailing seal pig 13 is a trailing liquid slug 24.

FIG. 1 illustrates the placement of the train of isolation tools, seal pigs, and liquid slugs within pipeline 10 as used in the process of conducting a hydrostatic test of the pipeline through a length of the pipeline designated as $D_2$ that contains test liquid slug 20. This length $D_2$ could be a little as a few feet, such as testing a weld joint or a single joint of pipe, or can be as much as several miles. To hydrostatically test the pipeline through the length of $D_2$ it is necessary to increase the hydrostatic pressure of the test liquid slug 22. In order to do this, two small pipe nipples 26A and 26B are affixed to the exterior of the pipeline and the pipeline is hot tapped to provide access to the interior. Nipples 26A and 26B are welded to the pipeline to either side of lead isolation tool 14. After the nipples are welded to the pipeline, by the use of hot tapping equipment, such as is available from T.D. Williamson, Inc. of Tulsa, Okla., holes are drilled through the pipe wall and into the interior of pipe 10. Thereafter piping 28A and 28B can be affixed to the pipe nipples 26A and 26B to connect to a pumping manifold 30. By means of a pump within manifold 30 test media liquid can be extracted from leading liquid slug 20 and pumped into test liquid slug 22 thereby raising the hydrostatic pressure in the test liquid slug. Within piping manifold 30 instrumentation is provided to measure and record the pressure applied to test liquid slug 22 which represents the hydrostatic pressure applied to section $D_2$ of the pipeline. The instrumentation within pumping manifold 30 can include facilities for measuring and recording the maximum pressure to which the pipe section $D_2$ is subjected. Further, after a predetermined pressure is applied to test liquid slug 22, pressure can be maintained for a period of time and a record made as to whether the pressure decreases indicating whether there is a leak in the pipe section $D_2$.

After completing the hydrostatic testing of pipe section $D_2$ by pumping fluid from leading liquid slug 20 into test liquid slug 22 and making a record of fluid pressure measurements, the pressure can be relieved by allowing fluid flow back into slug 20. The pipe nipple 26A and 26B can then be closed and the pumping manifold and piping 28A and 28B can be removed. Thereafter, the entire train of equipment illustrated in FIG. 1 can be moved along by releasing the gripper and packer modules making up each of the isolation tools 14 and 16.

Figure 7:
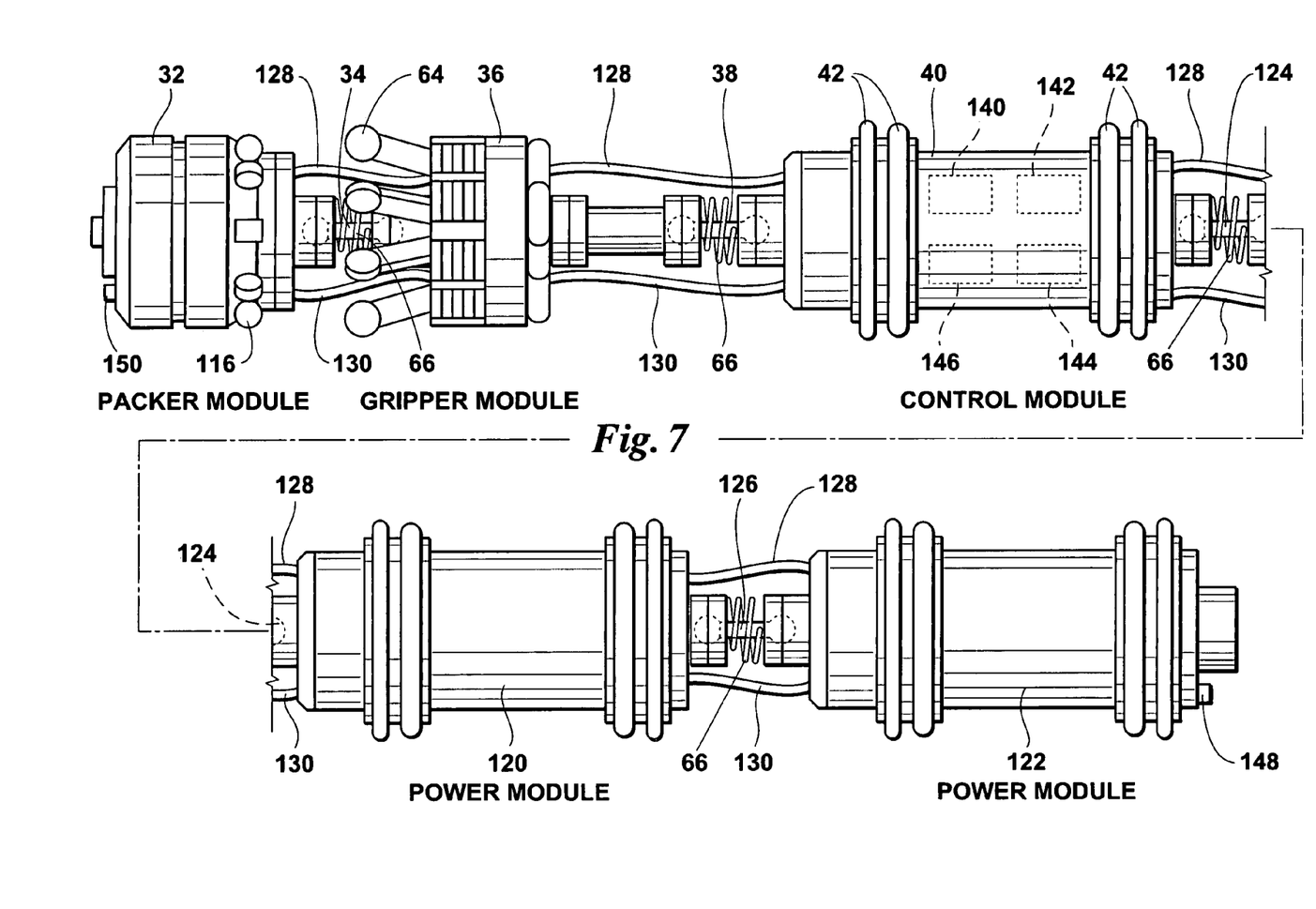

FIG. 7 illustrates one embodiment of an isolation tool. In the embodiment of FIG. 7, a packer module 32 is shown connected by universal joint 34 to a gripper module 36. Gripper module 36 is, in turn, connected by a universal joint 38 to a control module 40.

Each of the isolation tools 14 and 16 provides a system for closing fluid flow through the interior of a pipeline 10. The isolation tools are transported through pipeline 10 by the force of fluid flow. Each isolation tool can be remotely controlled to grip the interior of the pipeline to stop travel through the pipeline and remotely controlled to form a seal that terminates fluid flow. This type of tool is known in the industry as an "isolation tool" since it can be used to isolate portions of a pipeline.

Isolation tools 14 and 16 each includes instrumentation that is utilized to react to a remote signal to cause the tool to set itself in a selected position within pipeline 10. This instrumentation is well known in the pipeline industry and is not part of the invention herein. Stated another way, the invention herein is not concerned with the electronics by which isolation tools 14 and 16 are remotely controlled by means from exterior of the pipeline but is concerned with systems and methods of making use of such tools for hydrostatic testing pipelines.

In FIG. 1, isolation tools are indicated generally by the numerals 14 and 16. An example of an isolation tool is illustrated in more detail in FIG. 7. As illustrated in this figure the isolation tool is in the form of a train of components flexibly coupled together and configured to travel within a pipeline as a unit and for isolating a portion of the pipeline by closing off fluid flow through it. The isolation tool as shown in FIG. 7 includes, as major components thereof, a packer module 32, a grip module 36 and a control module 40. The rearward end of the packer module 32 is attached to the forward end of gripper module 36 by a ball joint 34. The rearward end of grip module 36 is secured to the forward end of control module 40 by a ball joint 38. Ball joints 34 and 38 are representative of mechanical means of flexibly connecting the basic elements of the isolation tool to each other so that the tool can move around bends in a pipeline without putting stress on the individual connected components.

Control module 40 includes a housing which is typically tubular as indicated with closed ends and in which the forward closed end includes a portion of ball joint 38. Positioned on the exterior of the tubular housing are radially extending elastomeric discs 42 that have exterior diameters that are less than that of the pipeline (not shown in FIG. 7) in which the isolation tool is employed. Discs 42 function essentially to support the control module centrally within the interior of a pipeline and to slidably seal against a pipeline interior wall.

Within control module 40 there is electronic instrumentation that functions in accordance with known techniques familiar to those in the pipeline pigging and isolation tool industry by which signals can be received from the exterior of a pipeline. Hydraulic control compartment controls the application of hydraulic fluid pressure to gripper module 36 and packer module 32.

Figure 5:
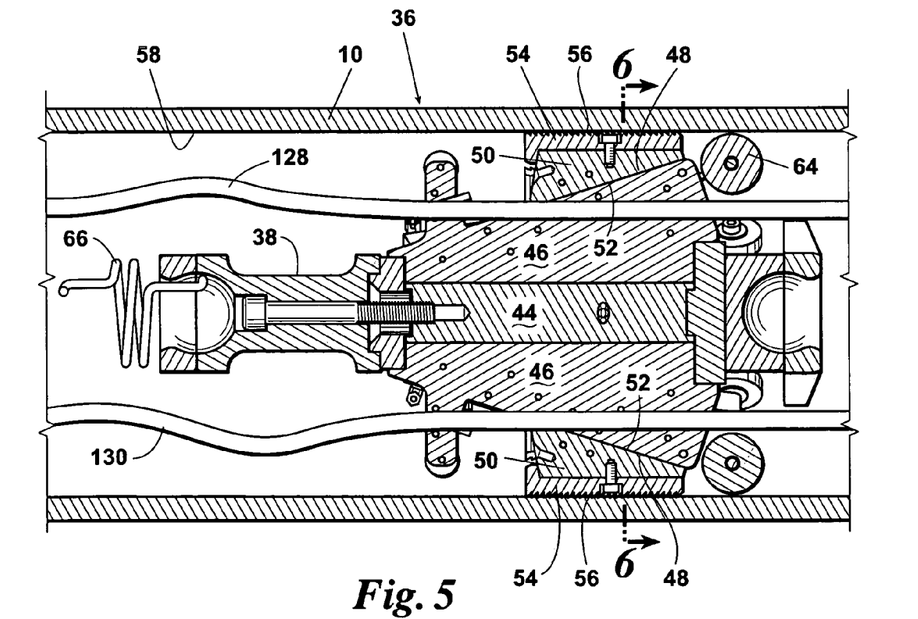
FIG. 5 is a cross-sectional view of a gripper module such as taken along the line 5-5 of FIG. 1 and also shows fluid transfer piping.
Figure 6:
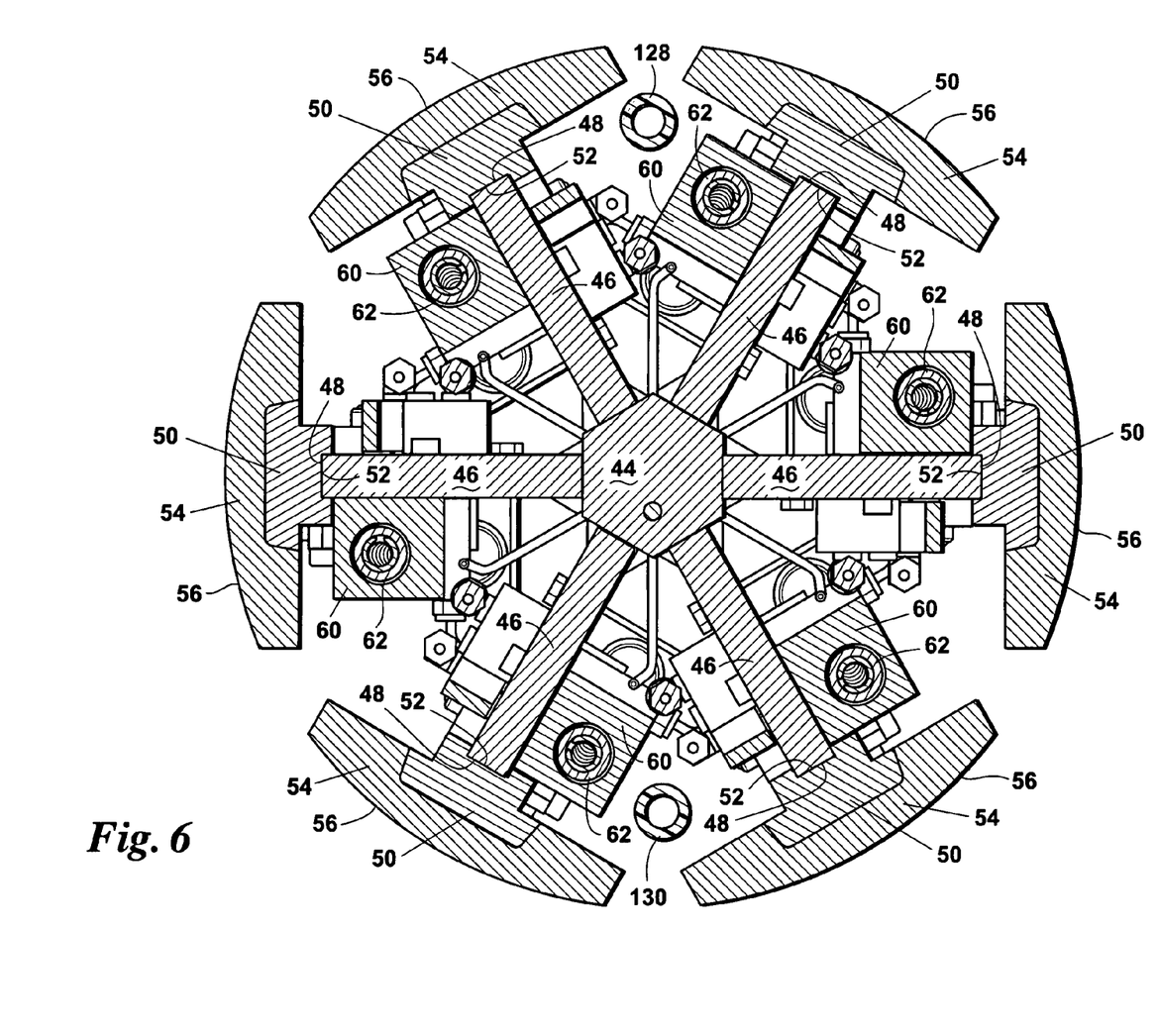

An example of a grip module as used in the isolation tool of this invention is illustrated in FIGS. 5 and 6. FIG. 5 shows a pipeline 10 in which grip module 36 is positioned. Grip module 36 includes an elongated central body frame member 44 that is shown to be of hexagonal cross-section in FIG. 6. Radially extending from frame member 44 are six radially extending rails 46. Each of rails 46 is in the form of a flat metal plate with a rail edge 48 that is inclined relative to the central body longitudinal axis. Slidably received on each rail edge 48 is a grip saddle 50, each having an inclined edge 52 that slides on a rail edge 48. Affixed to each of the grip saddle 50 is a grip shoe 54 that has a serrated surface as seen in FIG. 5 to non-slidably engage pipeline interior wall 58. The angular relationship between rail edge 48 and grip saddle inclined edge 52 is such that the grip shoe surface 56 engages the pipeline interior surface 58 in a parallel relationship.

Secured to a side wall of each of rails 46 is an actuator body 60, seen in FIG. 6, each of which slidably supports a double ended piston 62. An intermediate portion of each piston 62 is secured to a grip saddle 50 so that the displacement of each grip saddle and in turn each grip shoe 54 that slides on an edge 48 of each rail 46 is controlled by a piston 62. Each of the actuator bodies 60 includes an actuating cylinder. When pressure is applied to the actuating cylinders, pistons 62 function to move the grip saddles 50 and thereby grip shoes 54 in the direction towards or away from pipeline interior wall 58.

It is important that the grip shoes 54 are not in engagement with the interior surface of pipeline, such as surface 58 as seen in FIG. 5, as the isolation tool moves through the pipeline prior to reaching a point where closure of the pipeline is required. For this reason the grip module 36, as seen in FIG. 5, includes wheels 64 that roll along the interior surface of the pipeline.

As seen in FIG. 7, grip module 36 is connected at its rearward end to ball joint 38 that is positioned between the grip module and control module 40. As a part of each of ball joints 34 and 38 as seen in FIG. 7 a coiled spring 66 is employed for the purposes of preventing relative rotation between the components making up the isolation tool train.

Figure 4:
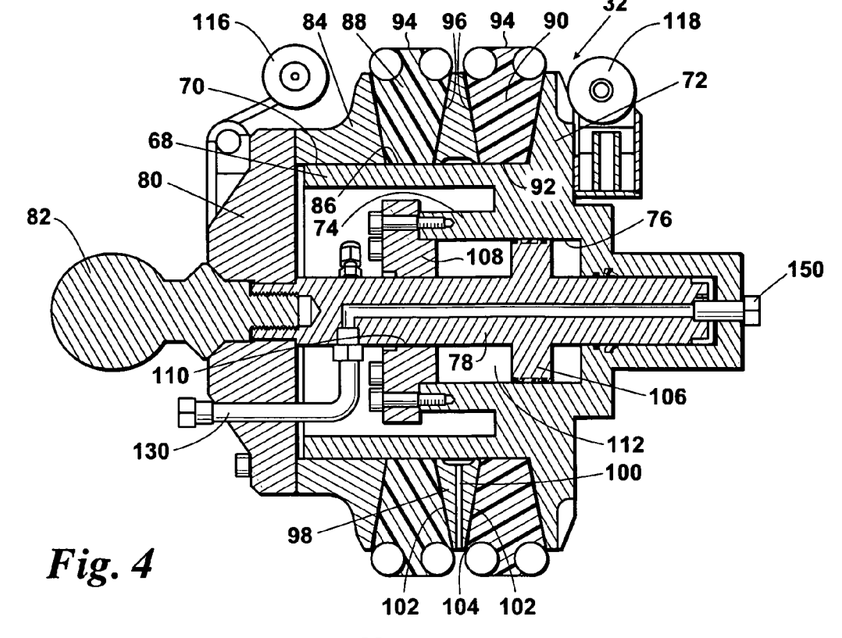

An embodiment of a packer module, indicated by the numeral 32 in FIG. 7, is illustrated in the cross-sectional view of FIG. 4. Packer module 32 includes a tubular body 68 having an external cylindrical surface 70 and, at one end thereof, a radially extending fixed forward flange 72. The tubular body 68 includes a portion defining a cylinder wall 74 with an internal cylinder surface 76. Centrally received within cylindrical surface 76 is a double ended piston rod 78. Secured to a rearward end of piston rod 78 is a radially extending rearward flange 80. Piston rod 78 has a threaded opening in the rearward end thereof that receives a threaded end of a ball joint 82. Rearward flange 80 is captured between the rearward end of piston rod 78 and ball joint 82. Secured to a forward surface of rearward flange 80 is a backup flange 84 that is slidably received on external cylindrical surface 86. Backup flange 84 is opposed to fixed forward flange 72.

Received on external cylindrical surface 86 is a first elastomeric packer 88 and an identical second elastomeric packer 90. Each of the elastomeric packers 88 and 90 is, in radial cross-section, frusto-conical, that is, each has sloped wall surfaces. Each of the elastomeric packers have an internal cylindrical surface 92 that is slidably positioned on external cylindrical surface 86. Each of the elastomeric packers has an outer pipe wall contacting surface 94 and opposed side wall surfaces 96.

Slidably received on tubular body external cylindrical surface 70 is a backup ring 98 having opposed sidewalls 102 that taper towards an outer circumferential surface 104. Side wall surfaces 102 of backup ring 98 mirror the side wall surfaces 96 of elastomeric packers 88 and 90.

Extending radially from piston rod 78 is a piston 106 having an outer cylindrical surface that sealably engages internal cylindrical surface 76.

Affixed at the rearward end of cylinder wall 74 is a cylinder head 108 having an opening 110 therein that slidably receives piston rod 78. Thus there is created within internal cylindrical wall 74 a cylindrical area 112 that, when pressure is applied thereto tends to move piston rod 78 forwardly towards the right, and consequently rearward flange 80 and backup flange 84 towards the right, to compress elastomeric packers 88 and 90 against forward flange 72. This action causes the outward displacement of the elastomeric packers so that the outer circumferential surfaces 94 thereof engage the interior wall of a pipeline to thereby close fluid flow through the pipeline. That is, when fluid pressure is applied to cylindrical area 112, as dictated by control module 40, elastomeric packers 88 and 90 are squeezed and radially outwardly expanded to close fluid flow through the pipeline.

To support the plugging module of FIG. 4, a number of rearward wheels 116 are employed. In the same way, forward wheels 118 support the forward end of the plugging module away from a pipeline internal wall as the isolation tool train moves through a pipeline.

The typical isolation tool as identified by tools 14 and 16 of FIG. 1 include, as a part thereof, as have been described, a control module 40 that typically includes a power source in the form of a battery. Further, the control module typically includes a hydraulic pump powered by battery power that is used to actuate the packer module 32 and gripper module 34. FIG. 7 illustrates a modified isolation tool that has each of the components as have been discussed with respect to FIG. 1 but, in addition, includes first and second auxiliary power modules 120 and 122. First power module 120 is connected to the rearward end of control module 40 by a universal joint 124 and second power module 122 is connected to the rearward end of first power module 120 by a universal joint 126. Power modules 120 and 122 are providing auxiliary and enhanced power, particularly battery power, for operating an on-board hydro-test pump or for the actuation of the other components making up an isolation tool. FIG. 7 illustrates flexible conduits 128 and 130. These flexible conduits interconnect the various elements of the isolation tool for purposes of supplying electrical energy and hydraulic fluid pressure from one component to another. For instance, one of the flexible conduits may be used to supply hydraulic pressure to actuate packer module 32 and gripper module 36. The flexible conduits can also be employed for providing electrical power from one unit to another such as electrical power from power modules 120 and 122 to a pump contained in control module 40. Further, one of the flexible conduits 128 and 130 of FIG. 7 may be employed for the transmission of pipeline liquids, such as liquid from leading liquid slug 20 passed lead isolation tool 14 and into the test liquid slug 22 as shown in FIG. 1. That is, one of the conduits 128 and 130 may be employed as required for hydrostatic testing the section of the length of the pipeline indicated by designation $D_2$ on FIG. 1.

Figure 2:
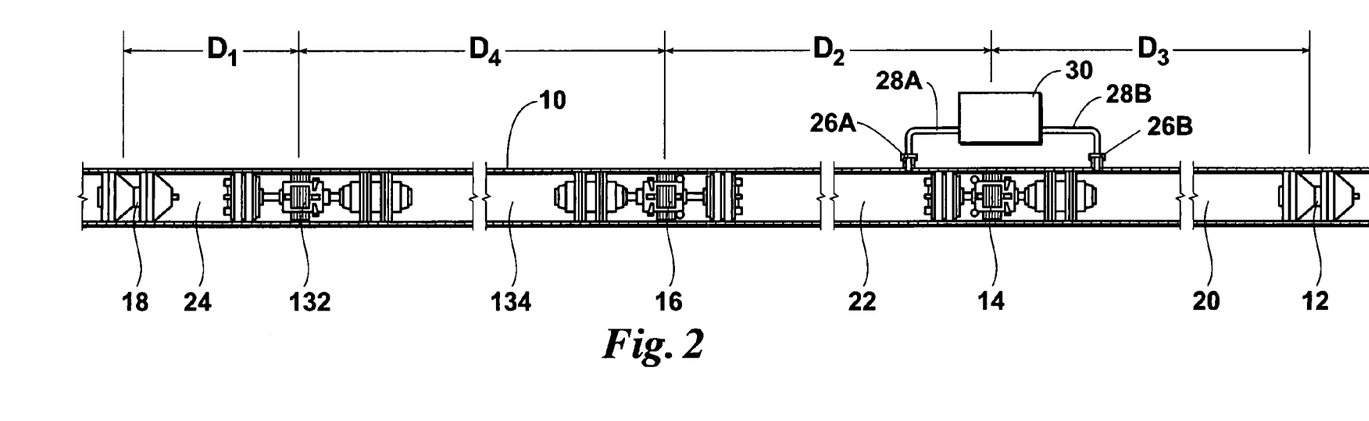

FIG. 1 of the drawings shows the use of two plugging pigs 14 and 16 to conduct a hydrostatic test of a length of pipe indicated by the designation $D_2$. FIG. 2 illustrates an alternate embodiment of the methods and systems of this invention that is particularly useful in the case of an operating pipeline where a defective section of the pipeline needs to be isolated from operating pressure during repair. In this case a third isolation tool 132 is employed. The third isolation tool 132 follows isolation tool 16 and is separated by a liquid slug 134.

The function of liquid slug 134 is to maintain a fixed distance behind second isolation tool 16 and to prevent a compressible gas bubble from seeping into the test liquid slug 22 that is contained between isolation tools 14 and 16. Thus, liquid slug 134 makes up an isolation section between isolation tools 16 and 132. In the arrangement of FIG. 2 the lead seal pig 12, lead liquid slug 20, lead isolation tool 14, first liquid slug 22, second isolation tool 16, trailing liquid slug 24, and trailing seal pig 18 functions for essentially the same purposes as described with respect to FIG. 1. In summary, the difference between FIGS. 1 and 2 is FIG. 2 provides an additional isolation tool 132 to provide for an isolation liquid slug section 134.

A main purpose of each of make-up medium slugs 20 and 24 is to provide make-up volumes to test liquid slug 22 during test preparation and to prevent a compressible gas bubble from seeping into either the test liquid slug 22 or the isolation liquid slug 134.

Another purpose of the trailing liquid slug 24 can be to carry a liquid, such as methanol or glycol, to allow drying of new or on-stream gas line while the pig train moves along. The test liquid slug 22 when hydrostatic testing a pipeline is nearly always water or mostly water and leaves a wet pipe wall which results in gradual loss of test slug volume as the train moves along the length of the pipeline. This trailing liquid slug which may also be termed a "make up liquid slug", then can serve the dual purpose of providing make-up liquid to isolation liquid slug 134 and drying the interior wall of the pipeline behind the test train.

Figure 3:
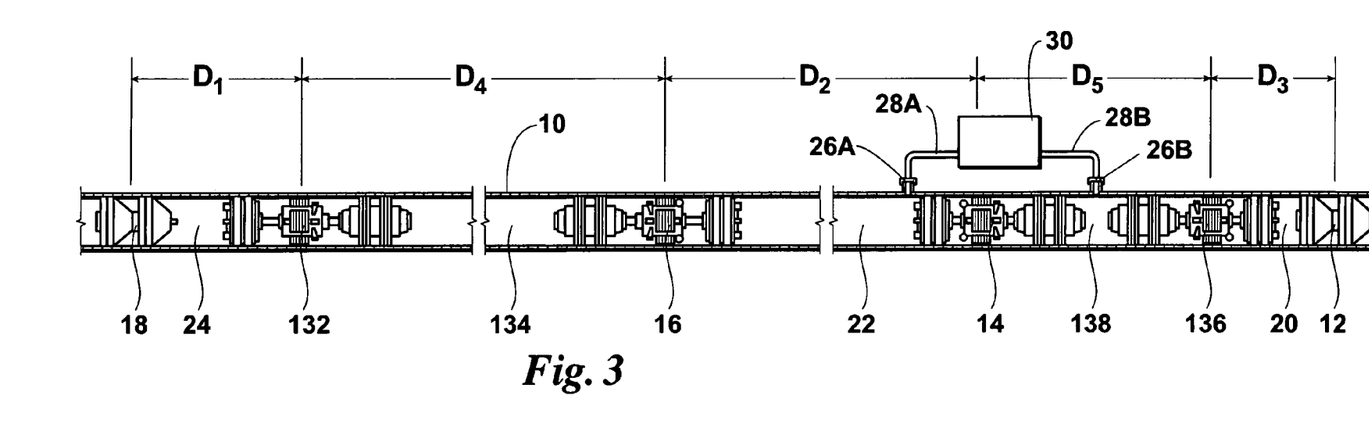
FIG. 3 is a diagrammatic cross-sectional view of a length of pipeline as in FIGS. 1 and 2 and showing a second alternate embodiment of the invention that employs four isolation tools, two seal pigs and five liquid slugs making up the pig train.

FIG. 3 shows an additional alternate embodiment of the systems and methods of this invention for hydrostatically testing a pipeline. FIG. 3 adds to FIG. 2 the use of an additional isolation tool, that is, a fourth isolation tool 136 that provides for a second isolation liquid slug 138 between it and isolation tool 14. Second isolation liquid slug 138 is supplementary to leading liquid slug 20 as described with reference to FIGS. 1 and 2 but, in addition, the fourth isolation tool 136 helps isolate the basic test system from the downstream pressure of an operating pipeline, in the event of a rupture in the test section, in order to prevent isolation tool 14 from being pushed toward the rupture resulting in damage to the tool.

As previously stated, pressure within test liquid slug 22 is provided by a pumping manifold 30 and piping 28A and 28B connected to pipe nipples 26A and 26B which are hot tapped onto the exterior of the pipeline 10. This system works satisfactorily when the pipeline 10 is on the earth's surface but represents a problem if the pipeline hydrostatic test section $D_2$ is on an ocean floor, that is, subsea or even if on the floor of a lake or river. For these applications test pumping pressure may be accomplished by on-board pumping capabilities provided by one or more of the isolation tools 14 and 16. As illustrated in FIG. 7, within control module 40 is instrumentation 140 which includes systems for measuring and recording the hydrostatic pressure applied to the pipe section $D_2$. Also included within control module 40 is an actuation hydraulic pump 142 to apply hydraulic fluid pressure to packer module 32 and gripper module 36 so these devices can be set and unset as dictated by signals conveyed from exterior of the pipeline. In addition, an isolation tool may contain, such as within control module 40, an on-board test pump 144 powered by an on-board battery 146. On-board test pump 144 is connected to draw liquid from leading slug 22 and pump this liquid past isolation tool 14 and into test liquid slug 22 to increase the hydrostatic pressure on the length of the pipeline $D_2$. This is accomplished without the use of pumping manifold 30, piping 28A and 28B and without the necessity of installing pipe nipples 26A and 26B. If the hydrostatic test section 22 is of relatively short length, such as if the length of this section was only sufficient to test a weld joint or a joint of pipe, then the power required to drive on-board test pump 144 could be supplied from on-board battery 146. On the other hand, if the length of pipeline $D_2$ that is being hydrostatic tested is relatively long, substantial additional power or energy source is required and thus, as is illustrated in FIG. 7, the use of auxiliary power modules 120 and 122 would likely be required. The number of power modules obviously can vary according to the quantity of fluid required to hydrostatically test pipeline section $D_2$ according to the volume thereof which is directly related to the internal diameter of the pipe and the length of the pipe section $D_2$.

Referring back to FIG. 7, if the hydrostatic fluid to be injected into test liquid slug 22 is to be moved by power supplied from within the pipeline, the test fluid can flow from a fluid inlet 148 on the rearward end of second power module 122, through flexible conduit 130 to a fluid outlet 150 on packer module 32. If auxiliary power modules 120 and 122 are not employed, fluid inlet 148 would typically be positioned on the rearward end of control module 40.

The invention thus provides a unique system that is in the form of a pig train made up of pipeline pig components that are moved by the force of fluid flow through the interior of a pipeline, which components include at least two isolation tools, at least one seal pig and a power pumping system for moving fluid under pressure into the interior of the length of the pipeline between the two isolation tools to hydrostatically test the pipeline. The system is adaptable for use to hydrostatically test pipelines on the earth's surface or in subsea environments.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A system for hydrostatic testing a selected section of a pipeline having fluid flow therethrough in an upstream to downstream direction, comprising:

a first isolation tool introduced into the pipeline having means for being propelled by fluid flow through the pipeline and having means by which the tool may be set at a first selected location and for sealing the pipeline against flow therepast;

a second isolation tool introduced into the pipeline a pre-selected time after the introduction of said first isolation tool and thereby a pre-selected distance upstream of said first isolation tool and having means for being propelled by fluid flow through the pipeline and having means for being set at a second selected location and for sealing the pipeline against flow therepast, spacing within the pipeline between said first and second isolation tools forming a test section and containing a test liquid slug;

a sealing pig introduced into the pipeline a pre-selected time or distance prior to said first isolation tool for being propelled by fluid flow in the pipeline and providing a leading slug of fluid in the pipeline between said first isolation tool and the sealing pig;

a pump for pumping fluid from said leading slug of fluid past said first isolation tool and into said test liquid slug to increase the hydrostatic pressure thereof; and instrumentation for measuring fluid pressure in said test liquid slug.

2. A system for hydrostatic testing a length of pipeline according to claim 1 wherein said pump is positioned exteriorly of the pipeline.

3. A system for hydrostatic testing a length of pipeline according to claim 2 including passageways formed in the wall of the pipeline upstream and downstream of said first isolation tool and piping communicating the passageways with said pump.

4. A system for hydrostatic testing a length of pipeline according to claim 1 wherein said pump is positioned interiorly of said pipeline.

5. A system for hydrostatic testing a length of pipeline according to claim 4 including a pump forming a portion of said first isolation tool having a liquid inlet communicating with said supply liquid slug and an outlet communicating with said test liquid slug.

6. A system for hydrostatic testing a length of pipeline according to claim 5 wherein said pump is powered by a battery source carried by said first isolation tool.

7. A system for hydrostatic testing a length of pipeline according to claim 6 including a power module forming a portion of said first isolation tool.

8. A system for hydrostatic testing a length of pipeline according to claim 1 wherein at least one of said isolation tools is in the form of a pipeline pig having a gripper component for locking the pipeline pig at a selected position in the pipeline and a packer component for stopping fluid flow through the pipeline.

9. A system for hydrostatic testing a length of pipeline according to claim 8 wherein said gripper component is actuated by a source of fluid pressure transported with said isolation tool.

10. A system for hydrostatic testing a length of pipeline according to claim 8 wherein said packer component is actuated by a source of fluid pressure transported with said isolation tool.

11. A system for hydrostatic testing a length of pipeline according to claim 8 wherein said isolation tool includes a control module component containing mechanisms for actuation of said gripper and packer components.

12. A system for hydrostatic testing a length of pipeline according to claim 1 including a trailing supply liquid slug and a trailing seal pig upstream of said second isolation tool.

13. A system for hydrostatic testing a length of pipeline according to claim 12 wherein said trailing supply liquid slug is formed of a liquid desiccant for use in drying the interior of the pipeline.

14. A system for hydrostatic testing a length of pipeline according to claim 1 including a third isolation tool upstream of said second isolation tool and an isolation liquid slug between the third isolation tool and said second isolation tool.

15. A system for hydrostatic testing a length of pipeline according to claim 14 including a fourth isolation tool positioned between said lead seal pig and said first isolation tool and including a second isolation liquid slug between the fourth isolation tool and said first isolation tool.

16. A method of hydrostatic testing a selected section of a pipeline having fluid flow therethrough in an upstream to downstream direction, comprising:
introducing into the pipeline a pig train made up of and in order a leading seal pig, a supply liquid slug, a first isolation tool, a test liquid slug and a second isolation tool;
permitting said pig train to traverse the pipeline interior by the force of fluid flow until said first isolation tool is downstream of and said second isolation tool is upstream of the selected selection of the pipeline to be tested;
stopping the traverse of the pig train by control of flow in the pipeline;
setting the isolation tools in position by applying exteriorly of the pipeline signals to actuate said isolation tools to each engage and seal the interior of the pipeline trapping said test liquid slug therebetween thereby forming a hydro-test section; and
pumping liquid from said supply liquid slug into said test liquid slug to a hydrostatic testing pressure.

17. A method of hydrostatic testing a selected section of a pipeline according to claim 16 wherein said step of pumping liquid from said supply liquid slug is accomplished exteriorly of the pipeline.

18. A method of hydrostatic testing a selected section of a pipeline according to claim 17 including the step of forming passageways in the wall of the pipeline upstream and downstream of said first isolation tool through which fluid can be passed from said supply liquid slug to said test liquid slug to increase the hydrostatic pressure thereof.

19. A method of hydrostatic testing a selected section of a pipeline according to claim 16 wherein said step of pumping liquid from said supply liquid slug is accomplished interiorly of the pipeline.

20. A method of hydrostatic testing a selected section of a pipeline according to claim 19 wherein the step of pumping liquid from said supply liquid slug includes using a pump forming a portion of said first isolation tool having a liquid inlet communicating with said supply liquid slug and an outlet communicating with said test liquid slug.

21. A method of hydrostatic testing a selected section of a pipeline according to claim 20 including the step of powering said pump by a battery source carried by said first isolation tool.

22. A method of hydrostatic testing a selected section of a pipeline according to claim 21 including the step of providing a power module to form a portion of said first isolation tool, the power module having said battery source therein.

23. A method of hydrostatic testing a selected section of a pipeline according to claim 16 wherein at least one of said isolation tools is in the form of a pipeline pig having a gripper module for locking at a selected position in the pipeline and a packer module for stopping fluid flow through the pipeline.

24. A method of hydrostatic testing a selected section of a pipeline according to claim 23 including the step of actuating said gripper module by a source of fluid pressure transported by said isolation tool.

25. A method of hydrostatic testing a selected section of a pipeline according to claim 23 including the step of actuating said packer module by a source of fluid pressure transported by said isolation tool.

26. A method of hydrostatic testing a selected section of a pipeline according to claim 23 including the step of actuating said gripper and packer modules by use of a control module forming a portion of said isolation tool.

27. A method of hydrostatic testing a selected section of a pipeline according to claim 16 including the step of providing a trailing supply liquid slug and a trailing seal pig upstream of said second isolation tool.

28. A method of hydrostatic testing a selected section of a pipeline according to claim 27 wherein said trailing supply liquid slug is formed of a liquid desiccant for use in drying the interior of the pipeline.

29. A method of hydrostatic testing a selected section of a pipeline according to claim 16 including the steps of providing in said pig train a third isolation tool and an isolation liquid slug between the third isolation tool and said second isolation tool serving to reduce the possibility of movement and/or damage to said second isolation tool in the event of failure of said hydro-test section.

30. A method of hydrostatic testing a selected section of a pipeline according to claim 29 including the steps of providing in said pig train a fourth isolation tool positioned between said lead seal pig and said first isolation tool and a second isolation liquid slug positioned between the fourth isolation tool and said first isolation tool serving to reduce the possibility of movement and/or damage to said first isolation tool in the event of failure of said hydro-test section.

31. A method of hydrostatic testing a selected section of a pipeline according to claim 16 wherein the hydrostatic testing pressure is less than a pipeline environmental hydrostatic pressure.

32. A method of hydrostatic testing a selected section of a pipeline according to claim 31 including the step of monitoring a test fluid pressure over a selected length of time, an increase indicating a subsea leakage in the pipeline.

33. An isolation tool for use in a pipeline having upstream and downstream directions, comprising:
    a pig body assembly slidably receivable within the pipeline and configured for movement through the pipeline by fluid flow;
    a controllable gripper portion for non-slidably engaging the pipeline;
    a controllable packer portion having expandable sealing surfaces for sealably engaging and closing fluid flow through the pipeline;
    a controllable cylindrical fluid passageway through said pig body assembly communicating with the upstream and downstream directions of the pipeline, said fluid passageway connecting the upstream and downstream directions of the isolation tool so that a total volume of fluid provided by said passageway and residing between the upstream and downstream directions of said isolation tool at any time "t" as a result of said passageway does not exceed a total volume of said passageway; and
    a pump for selectably moving fluid between the pipeline upstream and downstream directions through said fluid passageway.

34. An isolation tool according to claim 33 wherein said packer portion also serves as said gripper portion.

35. An isolation tool according to claim 33 including:
    a battery transported with said pig body assembly providing an energy source for said pump.

36. An isolation tool according to claim 35 wherein said battery is housed in a separate module forming a part of said pig body assembly.

37. An isolation tool according to claim 33 wherein said gripper portion, said packer portion and said pump portion are each controllable by signals eminating exteriorly of the pipeline.

38. An isolation tool according to claim 33 including:
    an instrument by which the hydrostatic pressure within the pipeline is measured.

39. An isolation tool according to claim 33 in which said pump is housed in a module forming a part of said pig body assembly.

40. An isolation tool according to claim 33 wherein said gripper and said packer are housed in separate modules forming parts of said pig body assembly.

41. An isolation tool according to claim 33 in which said pig body assembly is made up of a plurality of separate flexibly interconnected modules.

* * * * *